United States Patent
Sethi et al.

(10) Patent No.: US 6,969,256 B2
(45) Date of Patent: Nov. 29, 2005

(54) IMPRESSION JIG ASSEMBLY FOR USE WITH DENTAL IMPLANTS

(75) Inventors: Ashok Sethi, London (GB); Peter Sochor, Harrow (GB); Heiner Weber, Tübingen (DE)

(73) Assignee: Degussa Dental GmbH, Hanau (DE)

( * ) Notice: Subject to any disclaimer, the term of this patent is extended or adjusted under 35 U.S.C. 154(b) by 216 days.

(21) Appl. No.: 10/149,403

(22) PCT Filed: Dec. 15, 2000

(86) PCT No.: PCT/GB00/04834

§ 371 (c)(1),
(2), (4) Date: Jul. 30, 2002

(87) PCT Pub. No.: WO01/43659

PCT Pub. Date: Jun. 21, 2001

(65) Prior Publication Data

US 2003/0104336 A1    Jun. 5, 2003

(30) Foreign Application Priority Data

Dec. 15, 1999  (GB)  .................................... 9929662

(51) Int. Cl.⁷ ............................................... A61C 9/00
(52) U.S. Cl. ...................................... 433/173; 433/213
(58) Field of Search .............................. 433/172, 173, 433/174, 213

(56) References Cited

U.S. PATENT DOCUMENTS

| | | | |
|---|---|---|---|
| 5,106,300 A * | 4/1992 | Voitik ......................... | 433/173 |
| 5,350,297 A * | 9/1994 | Cohen ......................... | 433/76 |
| 5,538,426 A * | 7/1996 | Harding et al. ............. | 433/172 |
| 5,658,147 A * | 8/1997 | Phimmasone ............... | 433/213 |
| 6,155,828 A | 12/2000 | Lazzara et al. | |
| 6,213,773 B1 * | 4/2001 | Gittleman ................... | 433/172 |
| 6,283,752 B1 * | 9/2001 | Kumar ....................... | 433/172 |

FOREIGN PATENT DOCUMENTS

EP    727193    8/1996

* cited by examiner

Primary Examiner—Ralph A. Lewis
(74) Attorney, Agent, or Firm—Dennison, Schultz, Dougherty & MacDonald

(57) ABSTRACT

An impression jig assembly for coupling to a bone implant includes a split sleeve having co-axial upper and lower sleeve members, and a fixing screw for clamping the split sleeve to the implant. In use, the fixing screw passes through the split sleeve, and can be withdrawn once impression material has hardened around the assembly to allow the upper sleeve member to separate from the lower sleeve member.

9 Claims, 4 Drawing Sheets

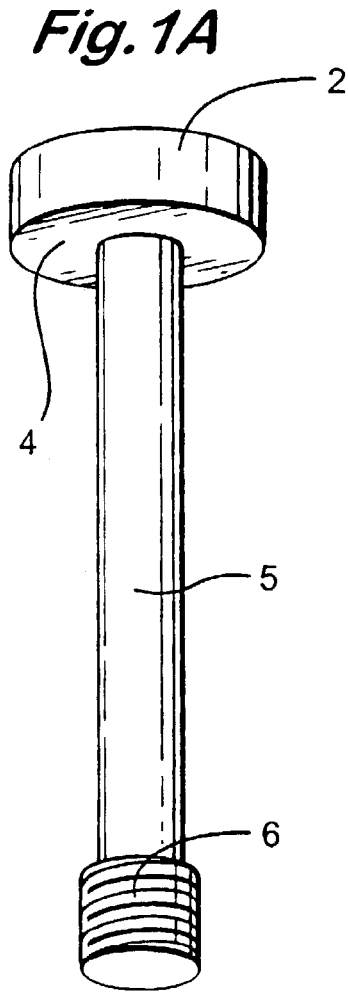
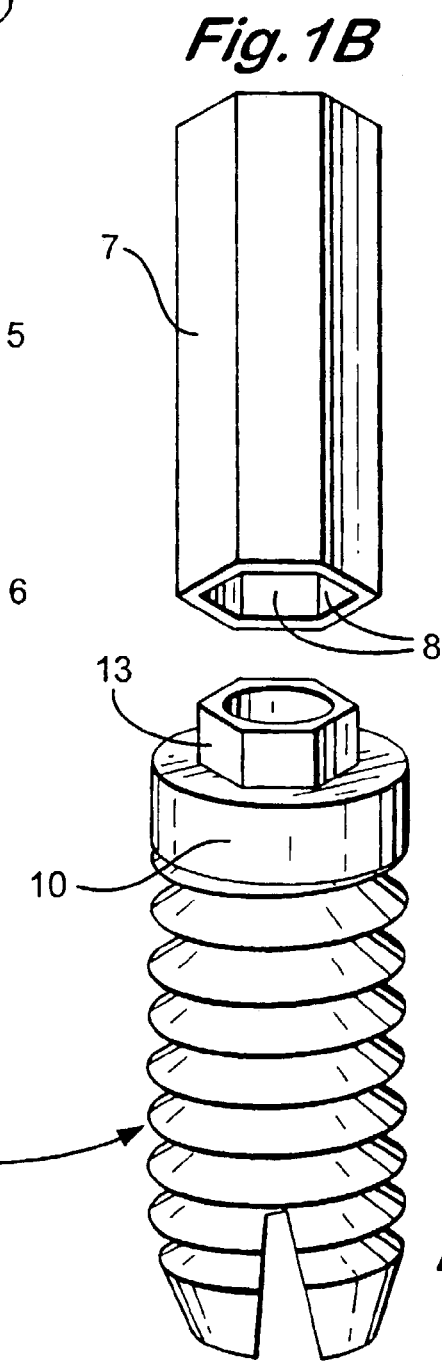
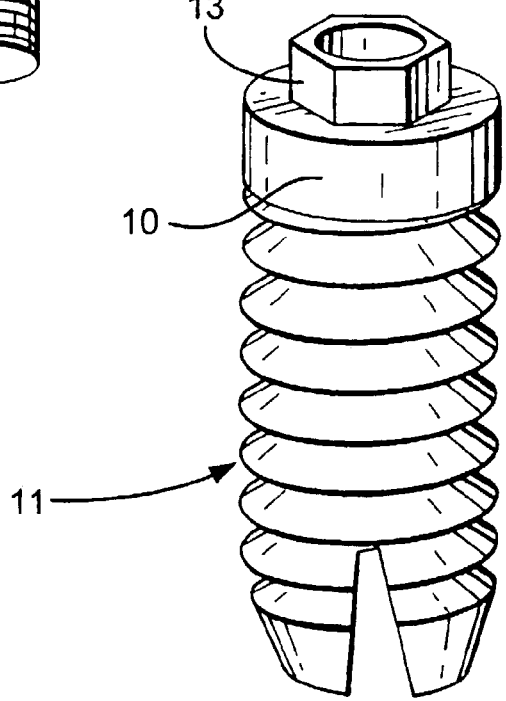
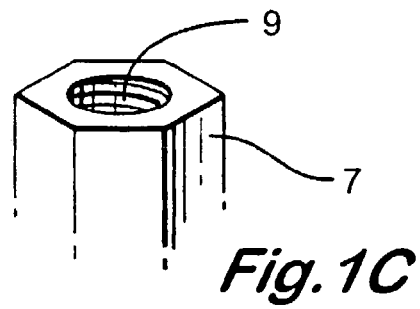
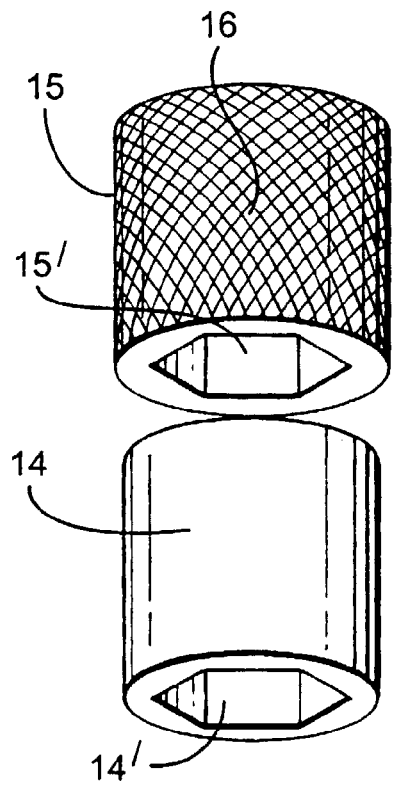

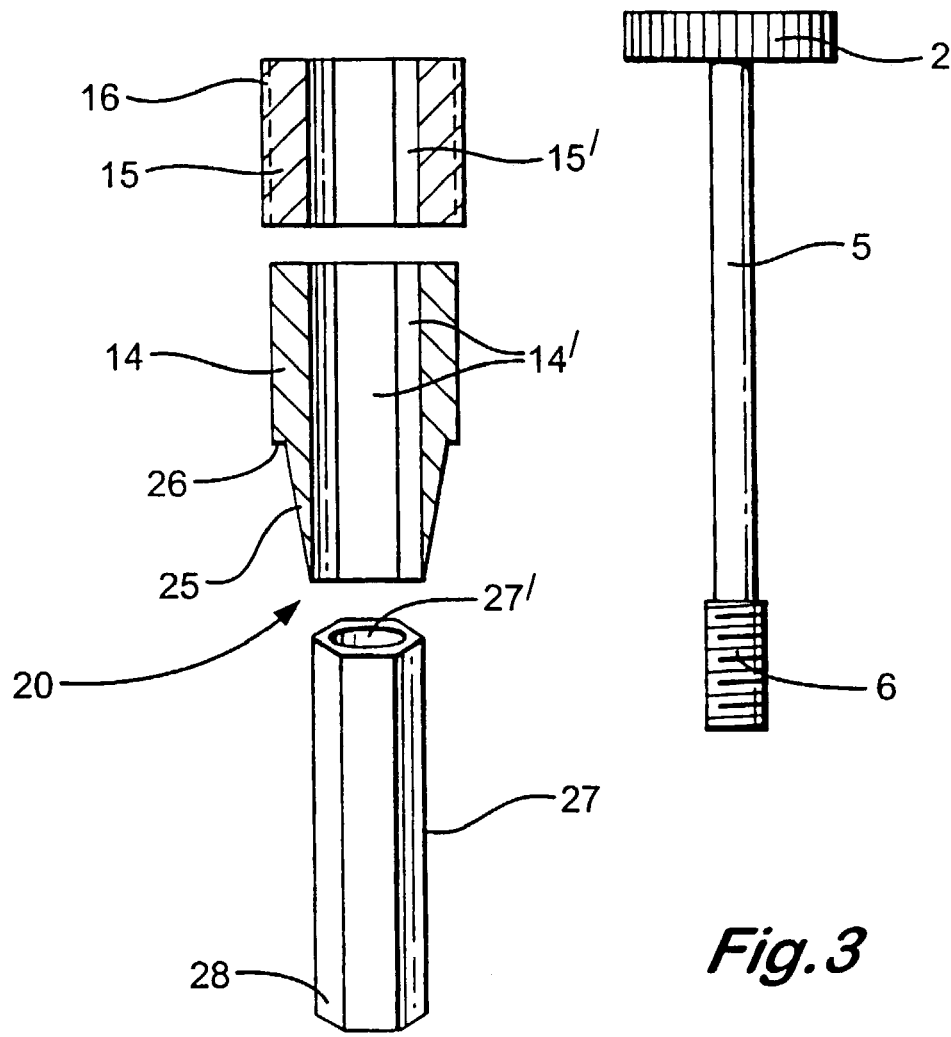
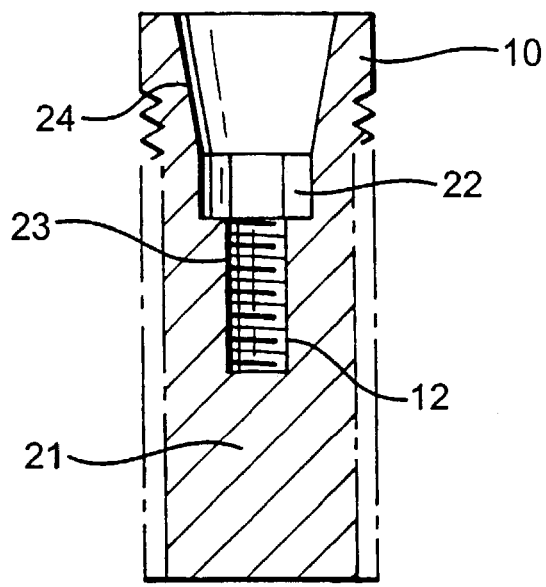
Fig.3

IMPRESSION JIG ASSEMBLY FOR USE WITH DENTAL IMPLANTS

The present invention relates to an impression jig assembly and particularly to an impression jig assembly suitable for use during dental implant surgery, as well as other reconstruction procedures.

When an impression is taken of the mouth or other part utilising a settable resin or other settable composition, it is often difficult to remove the impression from the mouth or other position on the body, particularly if more than one impression jig is utilised since the impression jigs tend to retain the impression in situ.

Previously this has been addressed by providing an implant with an internal bore which is provided with a plurality of internal driving flats and towards its open mouth a taper inclined to the plane of the axis of the implant at an angle of about 45°. The impression jig could then be secured by means of a elongate bolt or screw to the implant and removed after the impression has been taken with the hardened impression composition since it can readily separate from the implant itself.

The problem with such implants, which are hereinafter being referred to as "internally hexed implants", is that they are difficult to manufacture because the driving flats are relatively small and since these are used to rotate the implant during insertion into a blind bore during the initial stages of the process, it is desirable that the driving flats utilised have a larger diameter. Such implants are referred to as "externally hexed" implants.

BACKGROUND OF THE INVENTION

The result of using externally hexed implants is that it becomes difficult, if not impossible, to remove the impression jig after making an impression, especially when the implant is disposed at an angle to the direction of release of the impression. This is particularly so when more than one implant is involved. This is because utilising the previous technology is inappropriate because the external hex (driving flats) tends to impede the removal of the resultant impression because relative side-ways movement of the impression relative to the implant is precluded by virtue of the interengagement of the externally hexed implant and a sleeve in contact with it.

SUMMARY OF THE INVENTION

Accordingly the present invention provides an impression jig assembly comprising an inner sleeve terminating at a first end in a plurality of driving flats for engagement with corresponding members on an implant, a split outer sleeve adapted to engage with the external face of the inner sleeve, said outer sleeve comprising an upper and lower portion, and a fixing screw adapted to clamp the assembly to an implant, whereby in use the withdrawal of the fixing screw allows the inner sleeve to be withdrawn thereby allowing the upper portion of the outer sleeve to separate from the lower portion.

In a preferred form of the invention, the portion of the inner sleeve remote from the first end comprises a screw thread interengageable with a corresponding thread on the fixing screw. Thus by withdrawal of the fixing screw until the screw threads on the head of the inner sleeve and the end of the shaft of the fixing screw interengage, the inner sleeve may be withdrawn which allows the upper part of the outer sleeve to separate from the lower portion. Preferably the fixing screw is driven by means of an Allen key. It is desirable that the external face of the upper portion of the outer sleeve is knurled, whereas the lower portion is essentially plain.

Clamping action of the fixing screw may be achieved by providing that the flanged portion of the fixing screw extends over the upper ends of both the inner and outer sleeve. The engagement between the lower and outer sleeves is preferably a sliding interengagement of mutually shaped sleeves.

In an alternative form of the invention, the inner sleeve may comprise driving flats to its exterior lower portion at least. Preferably the inner sleeve has a number, often 6, of flat faces which in use cooperate with internal surfaces of the outer sleeve and the internal surfaces of a corresponding portion about a central bore of the implant thereby to provide a cooperative driving force on rotation. This arrangement relatively increases the diameter of the driving flats. In a particularly preferred embodiment the lower external portion of the lower outer sleeve is externally tapered and adapted to interfit with a corresponding portion about a central bore of the implant, the arrangement is such that the driving flats and cooperating tapers combine to drive the implant during rotation. It will be appreciated that the external driving flats also provide a locator means to prevent a rotation of an abutment and other component parts during implant finalisation.

In a further aspect of the present invention there is provided an impression jig assembly for coupling to a bone implant comprising:
a split sleeve having co-axial upper and lower sleeve members; and
a fixing screw for clamping the split sleeve to the implant, the fixing screw passing through the split sleeve, wherein in use withdrawal of the fixing screw allows the upper sleeve member to separate from the lower sleeve member.

BRIEF DESCRIPTION OF THE DRAWINGS

The invention will now be described, by way of illustration only, with reference to the accompanying drawings, which show:

FIG. 1A shows a fixing screw in plan from below;
FIG. 1B shows an inner sleeve in a side view from below;
FIG. 1C shows a view of the inner sleeve of FIG. 1B from slightly above;
FIG. 1D shows a side view of an implant in accordance with the present invention;
FIG. 1E shows upper and lower outer sleeve portions in side view from below;
FIG. 3 shows an exploded view in part cross-section of another embodiment of the invention.

DETAILED DESCRIPTION OF THE INVENTION

Figure 2:
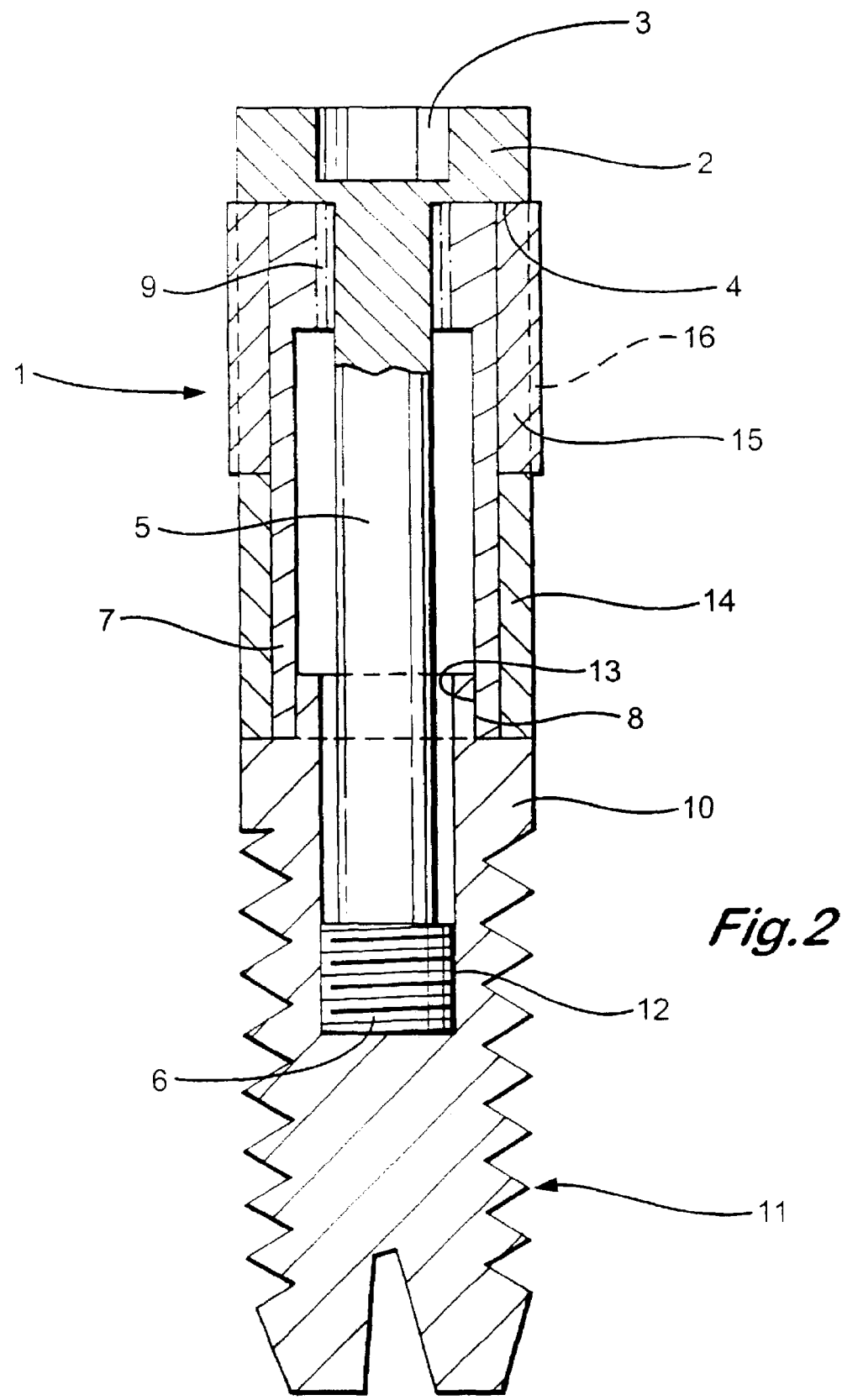
FIG. 2 shows a vertical cross-sectional view of the arrangements of FIG. 1 fully interengaged.

In FIGS. 1 and 2, an impression jig assembly 1 is provided with clamping screw head 2 comprising a flanged surface 4 for interengagement with upper ends of the inner and outer sleeves 7 and 15 respectively referred to later.

The clamping screw head 2 is provided with a perpendicular shank 5 terminating to its lower end in a screw thread portion of the shank 5 for purposes to be elucidated later.

The invention also provides an inner sleeve 7 of a generally hollow hexagonal configuration terminating at its lower edge in a plurality of driving flats 8 again of a hexagonal configuration. Inner sleeve 7 is provided with a lacuna or bore 8' extending throughout its length. Towards the upper end of the sleeve 7 is a screw thread portion 9.

Implant head 10 is provided with a plurality of driving flats 13 of a hexagonal configuration and adapted to interfit with the driving flat 8 on the internal sleeve 7. The implant 11 is provided with an axial blind bore provided with a threaded portion 12 for operative interconnection with the screw threaded portion 6 of the shank 5.

The assembly of the present invention is also provided with an outer, upper sleeve portion 15 and a lower outer sleeve portion 14, again with hexagonally arranged bores 14 and 15' of a size and shape such that they can cooperate in a sliding interengagement with the external face of the inner sleeve member 7.

In use of the embodiment of FIGS. 1 and 2 and as can be best seen from FIG. 2, implant 11 is secured in a bore in the jaw or other bone throughout the body (for example the facial bones during cancer surgery) etc. The implant 11 is then allowed to remain in the bore until bone overgrowth secures it in position. As has been described elsewhere, the hexagonal flats 13 are important in insuring that the implants all correctly aligned.

About six months after the implant 11 has been secured within the bone, it is necessary to take an impression of the site. Often this site is in the mouth and it is necessary to take an impression of the teeth on either side of a proposed tooth implant. In order to take this impression, utilising an externally hexed implant 11, it is necessary to use the arrangement shown in FIGS. 1 and 2. Thus, the clamping screw head 2 is assembled with an inner sleeve 7 and outer sleeves 14 and 15 as shown in FIG. 2. This is effected by means of a screw thread portion 6 entering the screw thread 12 of the implant 11 to secure the same. At this point the impression material may be formed over the impression jig and the surrounding site and allowed to harden. It is of course necessary for the clamping screw to be left proud of the impression composition so that it can be subsequently rotated.

After the impression material has hardened off, it is then necessary to remove the impression jig before removing the impression. This is done by removing the fixing screw 2 to a point where the screw thread portion 6 of the shank 5 interengage with the screw thread portion 9 of the inner sleeve 7 whereupon the inner sleeve 7 may be withdrawn along with the clamping screw head 2. Once the inner sleeve has been withdrawn, a certain amount of movement is possible but only between the lower end of the lower outer sleeve and the external driving flats 13, but also between the upper and lower portions of the outer sleeve. The impression may then be removed completely because the lower portion of the outer sleeve 14 can remain in situ at least substantially and the upper portion of the outer sleeve 15 can be removed along with the rest of the impression composition.

Although the lower portion of the outer sleeve 14 is shown as extending to possibly one half the length of the impression jig assembly, it may of course be significantly shorter with a commensurate increase in length of the upper portion of the outer sleeve. The upper portion of the sleeve may be knurled (16) at its upper portion for ease of adherence of the impression material.

With reference to FIG. 3 it will be noted that like members have like numbers as set out in FIGS. 1 and 2 above and thus it is that the fixing screw is generally identical and will not be described further.

The implant 21 is provided with an implant head 10 somewhat as in FIGS. 1 and 2 but otherwise the assembly 20 is somewhat differently configured.

The implant assembly 20 is provided with a downwardly inwardly directed taper 24 terminating in a plurality of driving flats 22, in this case of a generally hexagonal configuration. The driving flats 22 terminate towards their lower end in a threaded blind bore 23. The taper 24 makes it easier to interfit the parts together during use.

The assembly 20 also provides a sleeve 27 provided with a hollow but not necessarily hexagonal bore 27'. The lower portion of the hexagonal inner sleeve 27 cooperates with corresponding driving flat 22 in the implant in use and accordingly the inner sleeve 27, which is generally hexagonal throughout its axial length interfits with both the implant 21 and with the outer sleeves 14' and 15'.

The upper and lower portions of the outer sleeve have a slightly different configuration as those shown in FIGS. 1 and 2, in that the upper sleeve is smaller in an axial direction than the lower sleeve 14'. The lower portion of the outer sleeve 14' terminates in external inwardly directed taper 25 and optionally with a shoulder 26. It will be appreciated that the external taper 25 interfits with the corresponding internal taper 24 in the body of the implant 21.

In use, the shank of the fixing screw 5 passes through the bore of the inner sleeve 27 and the screw threaded portion of the shank 5 cooperates in the blind bore 23 so that rotation of the clamping screw head 2 causes the assembly to contract into the implant 21 in a fashion analogous to the arrangement shown in FIG. 2. As the clamping screw head 2 is tightened so the external driving flats 28 of the inner sleeve come into a sliding abutment with the driving surfaces 22 of the implant, while the tapered surfaces 25 of the lower portion of the outer sleeve and the taper of the implant 24 come into sliding cooperation such that a rotational driving force may be readily applied to the implant by means of rotation of the impression jig 20. The external driving flats 13 also provide a locator positioning for all subsequent parts e.g. abutments during the final stages of implant positioning.

Removal of the clamping screw head 2 along with the shank 5 allows the upper portion of the outer sleeve to be removed because the inner sleeve 27 can be removed with the clamping screw in a manner analogous to that described in FIGS. 1 and 2. For example inner sleeve may be removed by causing the screw thread portion 6 to engage with the screw thread portion 9 in the top of the inner sleeve as in FIG. 2. This allows an impression to be removed because it is not interengaged with the implant 21. Once the impression has been removed, the lower outer sleeve may be withdrawn.

Figure 4:
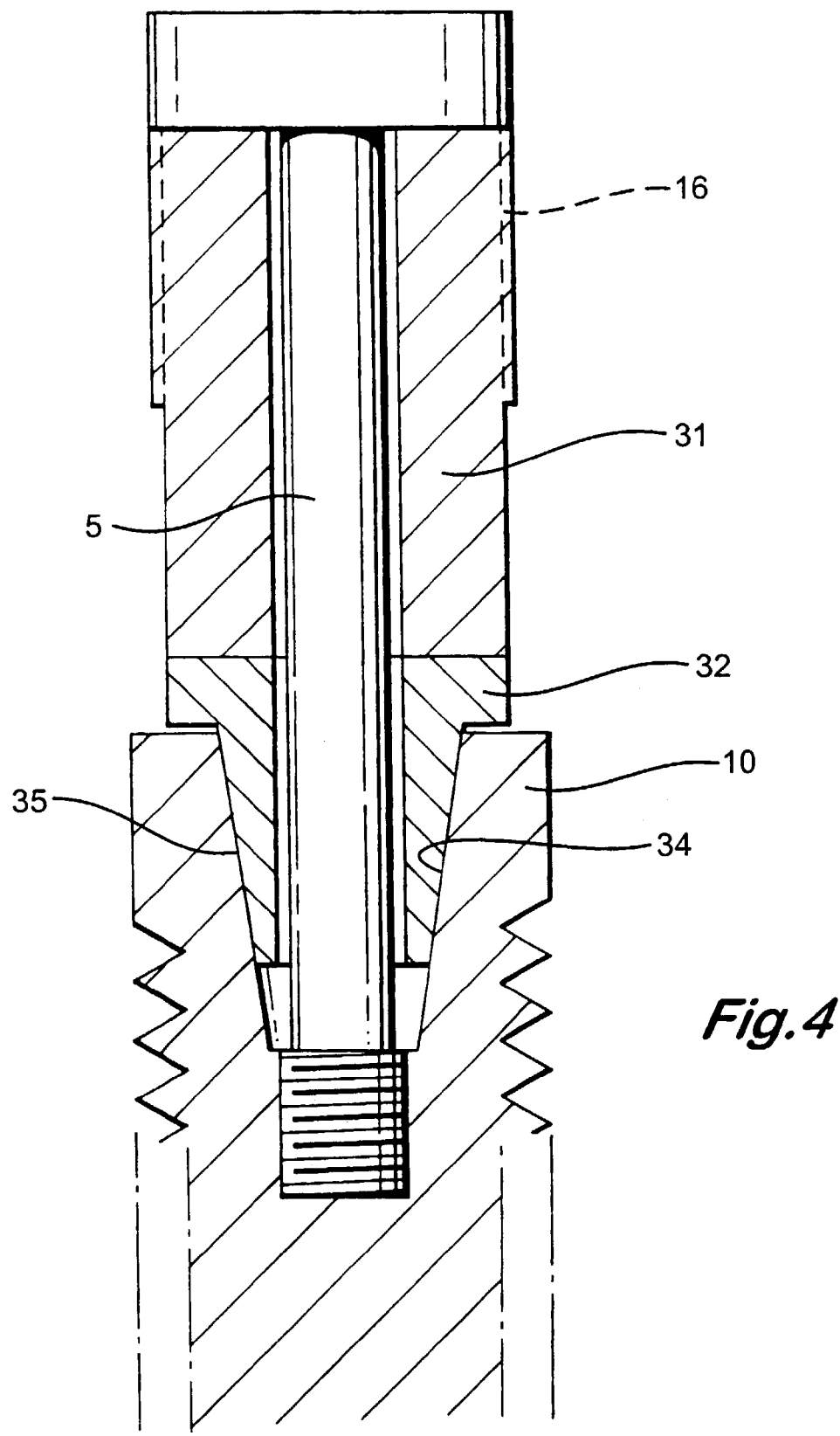
FIG. 4 shows a further embodiment of the present invention.

FIG. 4 shows a further assembly embodiment of the present invention. In this embodiment there are provided upper and lower sleeve members 31 and 32 which each have an axial bore through which fixing screw 5 passes. The lower sleeve member 32 tapers along coupling surface 34 so as to interengage with a corresponding tapering implant surface 35 on the implant 10. No inner sleeve is provided in this embodiment.

As before the assembly is coupled with the implant, in this case the combination of the co-operating tapering surfaces of the lower sleeve member and implant and the clamping action if the fixing screw 5 holding the assembly securely in place. Impression material is formed over the assembly, leaving the head of screw 5 clear so that it can be subsequently turned. When the impression material has hardened, the fixing screw 5, is removed thereby allowing the upper sleeve portion also to be removed with the impression. The lower sleeve portion remains in the implant.

It will be appreciated that whereas the impression jigs of the present invention are particularly useful for dental implant surgery, they are also useful in reconstructive applications where, for example, body parts are for one reason or another missing after accidents or significant surgery.

What is claimed is:

1. An impression jig assembly comprising an inner sleeve terminating at a first end in a plurality of driving flats for engagement with corresponding members on an implant;
   a split outer sleeve adapted for engagement with the external face of the inner sleeve;
   said outer sleeve comprising an upper and a lower portion; and
   a fixing screw adapted to clamp the assembly to said implant whereby in use withdrawal of the fixing screw allows the inner sleeve to be withdrawn thereby allowing the upper portion of the outer sleeve to separate from the lower portion.

2. An assembly according to claim 1 wherein the inner sleeve comprises at least one driving flat to its exterior lower portion for operative connection with a correspondingly shaped recess in the implant.

3. An assembly according to claim 2 wherein the inner sleeve has a central bore and a plurality of driving flats, the exterior configuration of said sleeve being generally unchanged throughout its external length.

4. An assembly accordingly to claim 2 wherein the lower external portion of the lower outer sleeve is externally tapered and adapted to interfit with the corresponding portion in the implant.

5. An assembly according to claim 1 wherein a portion of the inner sleeve remote from the first end comprises a screw thread interengageable with a corresponding thread on the fixing screw.

6. An assembly according to claim 1 wherein the fixing screw is driven by means of an Allen key.

7. An assembly according to claim 1 wherein the external face of the upper portion of the outer sleeve is knurled.

8. An assembly according to claim 1 wherein the clamping action of the fixing screw is achieved by providing a flanged portion of the fixing screw that extends over the upper ends of both the inner and outer sleeves.

9. An assembly according to claim 1 wherein the engagement between the inner and outer sleeves is sliding abutment.

* * * * *